US009867777B2

(12) United States Patent
Lee et al.

(10) Patent No.: US 9,867,777 B2
(45) Date of Patent: Jan. 16, 2018

(54) LIQUID FORMULATIONS FOR LONG-ACTING G-CSF CONJUGATE

(75) Inventors: Mi Ji Lee, Incheon (KR); Jae Min Lee, Seoul (KR); Byung Sun Lee, Seoul (KR); Sung Min Bae, Seongnam-si (KR); Se Chang Kwon, Seoul (KR)

(73) Assignee: Hanmi Science Co., Ltd. (KR)

( * ) Notice: Subject to any disclaimer, the term of this patent is extended or adjusted under 35 U.S.C. 154(b) by 0 days.

(21) Appl. No.: 13/574,039

(22) PCT Filed: Jan. 18, 2011

(86) PCT No.: PCT/KR2011/000369
§ 371 (c)(1),
(2), (4) Date: Jul. 19, 2012

(87) PCT Pub. No.: WO2011/090305
PCT Pub. Date: Jul. 28, 2011

(65) Prior Publication Data
US 2012/0294829 A1    Nov. 22, 2012

(30) Foreign Application Priority Data
Jan. 19, 2010   (KR) .................. 10-2010-0004839

(51) Int. Cl.
A61K 9/00     (2006.01)
A61K 38/19    (2006.01)
A61K 47/12    (2006.01)
A61K 47/26    (2006.01)
A61K 47/48    (2006.01)
C07K 14/535   (2006.01)
A61K 47/68    (2017.01)

(52) U.S. Cl.
CPC .......... *A61K 9/0019* (2013.01); *A61K 38/193* (2013.01); *A61K 47/12* (2013.01); *A61K 47/26* (2013.01); *A61K 47/6813* (2017.08); *A61K 47/6835* (2017.08); *C07K 14/535* (2013.01)

(58) Field of Classification Search
CPC ...... A61K 38/193; A61K 47/12; A61K 47/26; C07K 14/535
See application file for complete search history.

(56) References Cited

U.S. PATENT DOCUMENTS

| 5,919,757 A | 7/1999 | Michaelis et al. |
| 6,776,983 B1 | 8/2004 | Sumida et al. |
| 2005/0176108 A1 | 8/2005 | Kim et al. |
| 2008/0171857 A1 | 7/2008 | Komath et al. |

FOREIGN PATENT DOCUMENTS

| CA | 1341389 C | 10/2002 |
| CN | 1723220 A | 1/2006 |
| CN | 102740840 A | 10/2012 |
| CN | 103228672 A | 7/2013 |
| EP | 413622 A1 | 2/1991 |
| JP | H06008317 B2 | 2/1994 |
| JP | H06100593 A | 4/1994 |
| JP | H07135992 A | 5/1995 |
| JP | H07089952 B2 | 10/1995 |
| JP | H09511916 A | 12/1997 |
| JP | 2006-096765 A | 4/2006 |
| JP | 2006096765 A | 4/2006 |
| JP | 2007-531513 A | 11/2007 |
| JP | 2007531513 A | 11/2007 |
| JP | 2009501195 A | 1/2009 |
| KR | 910005624 B1 | 8/1991 |
| KR | 1993-0004597 B1 | 6/1993 |
| KR | 1019930004597 B1 | 6/1993 |
| KR | 10-1999-0009888 A | 2/1999 |
| KR | 100356140 | 10/2002 |
| KR | 1020040111351 A | 12/2004 |
| KR | 100560697 B1 | 3/2006 |
| KR | 100567902 B1 | 4/2006 |
| KR | 100596610 B1 | 7/2006 |
| KR | 10-2006-0108040 A | 10/2006 |
| KR | 1020060108040 A | 10/2006 |
| KR | 10-0725315 B1 | 5/2007 |
| KR | 100725314 B1 | 6/2007 |
| KR | 100725315 B1 | 6/2007 |
| KR | 100775343 B1 | 11/2007 |
| KR | 20100004839 A | 1/2010 |
| KR | 20110085917 A | 7/2011 |

(Continued)

OTHER PUBLICATIONS

Nagata, S. et al. Molecular cloning and expression of a cDNA for human granulocyte colony-stimulating factor. Nature, 1986, vol. 319, p. 415-418.*
Tsuchiya, M., et al. The chromosomal gene structure for murine granulocyte colony-stimulating factor. European Journal fo Biochemistry, 1987, vol. 165, p. 7-12.*
International Searching Authority, International Search Report for PCT/KR2011/000369 dated Sep. 21, 2011.
Korean Patent Office, Korean Office Action issued in corresponding KR Application No. 10-2011-0005161, dated Jan. 22, 2013.
Taiwanese Patent Office, Taiwanese Office Action issued in corresponding TW Application No. 101-2(5)01230, dated Dec. 20, 2012.
Chinese Patent Office, Chinese Office Action issued in corresponding CN Application No. 201180006430.9, dated Mar. 19, 2013.

(Continued)

*Primary Examiner* — Robert Landsman
*Assistant Examiner* — Bruce D Hissong
(74) *Attorney, Agent, or Firm* — Lerner, David, Littenberg, Krumholz & Mentlik, LLP

(57) ABSTRACT

Disclosed is a liquid formulation which allows long-acting G-CSF conjugates, that have improved in vivo duration and stability, to be stable when stored for a long period of time. It comprises a stabilizer composition characterized by buffer and mannitol. Being free of human serum albumin and other potential factors harmful to the body, the liquid formulation is free of concerns about viral infections and guarantees excellent storage stability to long-acting G-CSF conjugates.

17 Claims, 1 Drawing Sheet

(56) References Cited

FOREIGN PATENT DOCUMENTS

| KR | 20120045451 | A  | 5/2012 |
|----|-------------|----|--------|
| NO | 2005047334  | A1 | 5/2005 |
| NO | 2009027437  | A1 | 3/2009 |
| WO | 9315199     | A1 | 8/1993 |
| WO | 9315200     | A1 | 8/1993 |
| WO | 94/14466    | A1 | 7/1994 |
| WO | 199701580   | A1 | 1/1997 |
| WO | 199712977   | A1 | 4/1997 |
| WO | 97/24137    | A1 | 7/1997 |
| WO | 2005/014025 | A1 | 2/2005 |
| WO | 2005/047334 | A1 | 5/2005 |
| WO | 2005/047337 | A1 | 5/2005 |
| WO | 2009009562  | A2 | 1/2009 |
| WO | 2009/027437 | A1 | 3/2009 |

OTHER PUBLICATIONS

Japanese Patent Office; Japanese Office Action dated Dec. 24, 2013 issued in Japanese Application No. 2012-549939.
European Patent Office, Communication dated May 7, 2014, issued in corresponding European application No. 11734854.0.
Chinese Intellectual Property Office, communication Feb. 28, 2015 issued in corresponding Chinese application No. 2011800006430.9.
Clark et al., Science, 236:1229-1237, 1987.
Duncan et. al., Int. J. Pharm. 120: 179-188, 1995.
Geigert, John,J. Parenteral Sci. Tech, 43 (5): 220-224, 1989.
Nagata et al., EMBO J., 5(3): 575-581, 1986.
Nomura et aL, EMBO J. 5(5): 871-876, 1986.
Norde, Willem, Adv. Colloid Interface Sci., 25:267-340, 1986.
Sada et al., J. Fermentation Bioengineering 71:137-139, 1991.
Souza et al., Science, 232:61-65, 1986.
Tarelli et al., Biologicals, 26:331-346, 1998.
Wang, Int. J. Pharm. 185: 129-188, 1999.
Wong, David, Pharm. Tech., 34-48, 1997.
Chung et al., "Overproduction of Human Granulocyte-Colony Stimulating Factor Fused to the PeIB Signal Peptdie in *Escherichia coli*", Journal of Fermentation and Bioengineering, vol. 85, No. 4, pp. 443-446, Dec. 22, 1997.
Makrides, "Strategies for Achieving High-Level Expression of Gense in *Esherichia coli*", Microbiological Reviews, vol. 50, No. 3, pp. 512-538, Sep. 1996.
Perez-Perez et al., "DNAK/DANJ Supplementation Improves The Periplasmic Production of Human Granulocyte-Colony Stimulating Factor in *Escherichia Coli*", Biochemical and Biophysical Research Communiations, vol. 210, No. 2, pp. 524-529, May 16, 1995.
Yamaguchi et al., "Bioassay of Human Granulocyte Colony-Stimulating Factor Using Human Promyelocytic HL-60 Cells", Biol. Pharm. Bull., vol. 20, No. 9, pp. 943-947, Sep. 1997.

* cited by examiner

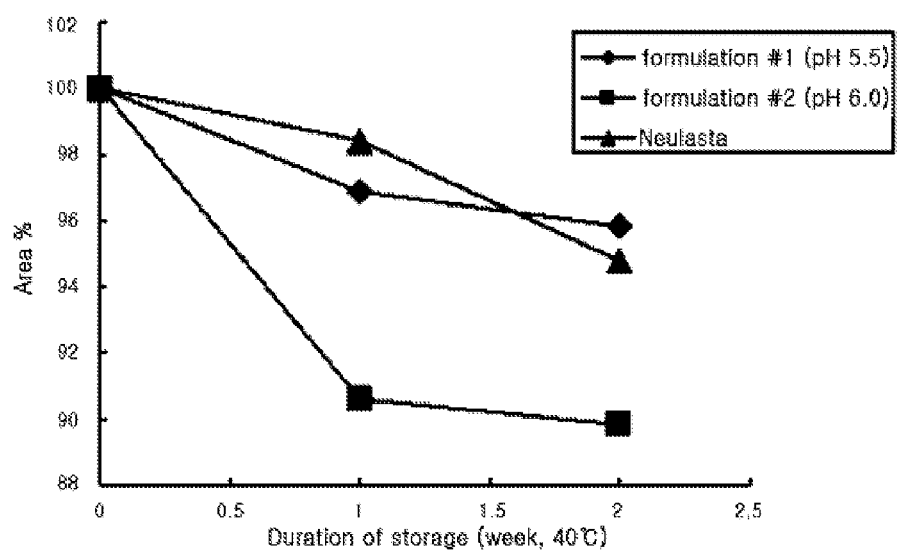

LIQUID FORMULATIONS FOR LONG-ACTING G-CSF CONJUGATE

CROSS REFERENCE TO RELATED APPLICATIONS

This application is a National Stage of International Application No. PCT/KR2011/000369 filed Jan. 18, 2011, claiming priority based on Korean Patent Application No. 10-2010-0004839, filed Jan. 19, 2012, the contents of all of which are incorporated herein by reference in their entirety.

TECHNICAL FIELD

The present invention relates to a liquid formulation for guaranteeing long-term storage stability of a long-acting G-CSF conjugate in which G-CSF, a non-peptide polymer and an immunoglobulin Fc fragment are covalently linked and which exhibits an extended duration of action compared to the wild-type.

BACKGROUND ART

Granulocyte-colony stimulating factor (G-CSF) is a cytokine that stimulates stem cells of bone marrow and leukocytes to induce them to differentiate and proliferate. It is a glycoprotein ranging in molecular weight from 18,000 to 19,000 Da with a pI of 6.1 (5.5-6.1 depending on the degree of glycosylation (Nomura et al., EMBO J. 5(5): 871-876, 1986).

Recombinant DNA technology discovered the molecular and genetic properties of G-CSF (Clark and Kamen, Science, 236:1229-1237, 1987). Since the cloning of human G-CSF gene from the cDNA libraries constructed with mRNAs isolated from CHU-2 and human bladder carcinoma 5637 cell lines (Nagata et al., Nature, 319: 415-418, 1986; Nagata et al., EMBO J., 5(3): 575-581, 1986; Souza et al., Science, 232: 61-65, 1986), recombinant DNA technology has allowed G-CSF to be produced from mammal cells and prokaryotes. In addition, the present inventors have found that a modified hG-CSF, which is different from the wild-type in that at least one amino acid residue, especially the cysteine residue at position 17 is substituted with a different amino acid residue, can be secreted in a form free of methionine residues at the N-terminus thereof on a large scale into a periplasm (Korean Patent No. 10-356140).

Since polypeptides tend to easily denature due to their low stability, be degraded by proteolytic enzymes in the blood and easily passed through the kidney or liver, protein medicaments, including polypeptides as pharmaceutically effective components, need to be frequently administered to patients to maintain the desired blood level concentrations and titers. However, this frequent administration of protein medicaments, especially by injection, causes pain in patients.

To solve these problems, a lot of effort has been put into improving the serum stability of protein drugs and maintaining the drugs in the blood at high levels for a prolonged period of time, and thus maximizing the pharmaceutical efficacy of the drugs. For use in long-acting formulations, protein drugs must be formulated to have high stability and have their titers maintained at sufficiently high levels without incurring immune responses in patients.

To stabilize proteins and prevent enzymatic degradation and clearance by the kidneys, a polymer having high solubility, such as polyethylene glycol (PEG), was conventionally used to chemically modify the surface of a protein drug. By binding to specific or various regions of a target protein, PEG stabilizes the protein and prevents hydrolysis, without causing serious side effects (Sada et al., J. Fermentation Bioengineering 71:137-139, 1991). However, despite its capability to enhance protein stability, PEGylation has problems such as greatly reducing the titers of physiologically active proteins. Further, the yield decreases with increasing molecular weight of the PEG due to the reduced reactivity of the proteins.

An alternative method for improving the in vivo stability of physiologically active proteins is by linking a gene of a physiologically active protein to a gene encoding a protein having high serum stability by genetic recombination technology and culturing the cells transfected with the recombinant gene to produce a fusion protein. For example, a fusion protein can be prepared by conjugating albumin, a protein known to be the most effective in enhancing protein stability, or its fragment to a physiologically active protein of interest by genetic recombination (PCT Publication Nos. WO 93/15199 and WO 93/15200, European Pat. Publication No. 413,622).

Another method is to use an immunoglobulin. As described in U.S. Pat. No. 5,045,312, human growth hormone is conjugated to bovine serum albumin or mouse immunoglobulin by use of a cross-linking agent. The conjugates have enhanced activity when compared with unmodified growth hormone. Carbodiimide or glutaraldehyde is employed as the cross-linking agent. Non-specifically bonding to the peptides, however, such low-molecular weight cross-linking agents do not allow the formation of homogeneous conjugates and are even toxic in vivo. In addition, the patent shows activity enhancement only thanks to chemical coupling with the growth hormone. The method of the patent cannot guarantee activity enhancement to various kinds of polypeptide drugs, so that the patent does not recognize even protein stability-related factors, such as duration, blood half-period, etc.

Recently a drug formulation has been suggested that is a long-acting protein drug formulation with improvement in both in vivo duration and stability. For use in the long-acting drug formulation, a protein conjugate is prepared by covalently linking a physiologically active polypeptide, a non-polypeptide polymer and an immonoglobulin Fc fragment (Korean Patent No. 10-0567902 and 10-0725315).

In this method, G-CSF can be used as a physiologically active polypeptide to afford a long-acting G-CSF conjugate. To apply long-acting G-CSF conjugates to drug products, it is necessary to maintain the pharmaceutical efficacy thereof in vivo while restraining physicochemical changes such as light-, heat- or additives-induced degeneration, aggregation, adsorption or hydrolysis during storage and transportation. Long-acting G-CSF conjugates are more difficult to stabilize than an G-CSF polypeptide itself because they are increased in volume and molecular weight.

Generally, proteins have a very short half life and, when exposed to unsuitable temperatures, water-air interfaces, high pressures, physical/mechanical stress, organic solvents, microbial contamination, etc., they undergo such degeneration as the aggregation of monomers, precipitation by aggregation, and adsorption onto the surface of containers. When degenerated, proteins lose their physicochemical properties and physiological activity. Once degenerated, proteins almost cannot recover their original properties because the degeneration is irreversible. Particularly in the case of the proteins that are administered in trace amounts of hundreds migrograms per injection, such as G-CSF, when they lose stability and thus are absorbed onto the surface of the container, a relatively great amount of damage results. In addition, absorbed proteins easily aggregate during a degeneration process, and aggregates of the degenerated proteins, when administered into the body, act as antigens, unlike proteins synthesized in vivo. Thus, proteins must be administered in a stable form. Many studies have been done to prevent the degeneration of proteins in solutions (John Geigert, J. Parenteral Sci. Tech., 43(5): 220-224, 1989; David Wong, Pharm. Tech., 34-48, 1997; Wei Wang., Int. J. Pharm., 185: 129-188, 1999; Willem Norde, Adv. Colloid Interface Sci., 25: 267-340, 1986; Michelle et. Al., Int. J. Pharm. 120: 179-188, 1995).

Lyophilization is applied to some protein drugs to achieve the goal of stability. However, lyophilized products are inconvenient in that they must be re-dissolved in injection water for use. In addition, they need massive investment on large-capacity freeze-driers because lyophilization process is included in the production processes thereof. The confrication of proteins by use of a spray drier was suggested. However, this method is economically unfavorable due to low production yield. Further, a spray-drying process exposes the proteins to high temperatures, thus having negative influences on the stability of the proteins.

As an alternative to overcome the limitations, stabilizers have appeared that, when added to proteins in solution, can restrain physicochemical changes of protein drugs and maintain in vivo pharmaceutical efficiency even after having been stored for a long period of time. Among them are carbohydrates, amino acids, proteins, surfactants, polymers and salts. Inter alia, human serum albumin has been widely used as a stabilizer for various protein drugs, with certification for its performance (Edward Tarelli et al., Biologicals, 26: 331-346, 1998).

A typical purification process for human serum albumin includes inactivating biological contaminants such as mycoplasma, prion, bacteria and virus or screening or examining one or more biological contaminants or pathogens. However, there is always the risk that patients are exposed to the biological contaminants because they are not completely removed or inactivated. For example, human blood from donors is screened to examine whether it contains certain viruses. However, this process is not always reliable. Particularly, certain viruses existing in a very small number cannot be detected.

Alternatives to human serum albumin have recently been suggested, including recombinant albumin (Korean Patent Laid-Open Publication No. 10-2004-0111351) and albumin-free G-CSF (Korean Patent Nos. 10-0560697 and 10-0596610).

Although employing stabilizers free of albumin, different proteins may be gradually inactivated due to the chemical differences thereof because they are subjected to different ratios and conditions during storage. The effect of a stabilizer on the storage term of proteins differs from one protein to another. That is, various stabilizers may be used at different ratios depending on physicochemical properties of the proteins of interest.

In addition, different stabilizers, when concurrently used, may bring about reverse effects due to competition and the erroneous operation thereof. A combination of different stabilizers also elicits different effects because they cause the proteins to change in characteristics or concentration during storage. Because each stabilizer suitably performs its stabilizing activity in a certain range of concentrations, many efforts must be made to combine the kinds and concentrations of different stabilizers, with care.

Particularly, as for long-acting G-CSF conjugates which are improved in in vivo duration and stability, their molecular weights and volumes are quite different from those of general G-CSF compounds because they are composed of the physiologically active peptide G-CSF and immunoglobulin fragment Fc. In addition, the stability of immunoglobulin Fc fragments varies highly depending on pH. Thus, conventional stabilizers for G-CSF cannot be employed as they are. Accordingly, stabilizers with special compositions different from those of stabilizers for G-CSF are required for long-acting G-CSF conjugates.

Leading to the present invention, intensive and thorough research into the development of the development of a stable liquid formulation for long-acting G-CSF conjugates, capable of retaining pharmaceutical efficacy for a long term without viral infection, resulted in the finding that a stabilizer comprising buffer in a certain pH range and a highly concentration of mannitol endows long-acting G-CSF conjugates with enhanced stability and allows the formation of economical and stable liquid formulations of long-acting G-CSF conjugates.

DISCLOSURE

Technical Problem

It is therefore an object of the present invention to provide a liquid formulation comprising a long-acting G-CSF conjugate in which G-CSF, a non-peptide polymer and an immunoglobulin Fc fragment are covalently linked, and an albumin-free stabilizer containing buffer and mannitol.

Technical Solution

In accordance with an embodiment thereof, the present invention provides a liquid formulation comprising a long-acting G-CSF conjugate in which G-CSF, a non-peptide polymer and an immunoglobulin Fc fragment are covalently linked, and an albumin-free stabilizer composed of buffer and mannitol.

The term "long-acting G-CSF conjugate" or, as used herein, is intended to refer to a protein construct in which the physiologically active G-CSF, one or more non-peptide polymers and one or more immunoglobulin Fc fragments are covalently linked, and which has a prolonged duration of action compared to G-CSF in its natural form.

The term "long-acting", as used herein, refers to a prolonged duration of action compared to that of a natural form. The term "conjugate" refers to a construct in which G-CSF, a non-peptide polymer and an immunoglobulin Fc fragment are covalently linked.

For use in the present invention, the G-CSF has an amino acid sequence of human G-CSF or closely related analogues. The G-CSF useful in the present invention may be a naturally occurring protein or a recombinant protein. Also, the G-CSF may be a mutant one that has undergone the insertion, deletion or insertion of amino acids provided that the mutation does not have a significant influence on the original biological activity thereof.

Human G-CSF or its analogues useful in the present invention may be isolated from vertebrates or may be chemically synthesized. Alternatively, G-CSF or its analogues may be obtained from prokaryotes or eukaryotes which are transformed with a gene encoding G-CSF or its analogue using a genetic recombination technique. In this regard, colon bacteria (e.g., *E. coli*), yeast cells (e.g., *S. cerevisiae*), or mammalian cells (e.g., Chinese hamster ovarian cells, monkey cells) may be used as host cells. Depending on the host cells, the recombinant G-CSF or its analogues may be glycosylated with mammalian or eukaryotic carbohydrates or aglycosylated. When expressed, the recombinant G-CSF or its analogues may contain the initial methionine residue (position −1). Preferably, recombinant human G-CSF (HuG-CSF) is prepared using CHO cells as a host. The recombinant human G-CSF (HuG-CSF) prepared using *E. coli* as a host cell is suitable for the present invention. In a preferred embodiment of the present invention, the recombinant human G-CSF is a mutant one ($^{17}$Ser-G-CSF) in which a serine residue was located at position 17, instead of cysteine for the wild-type, and could be expressed as disclosed in Korean Patent No. 10-356140.

For use in the present invention, the immunoglobulin Fc fragment has an amino acid sequence of human immunoglobulin Fc fragments or their closely related analogues. The Fc fragments may be obtained from native forms isolated from animals including cows, goats, swine, mice, rabbits, hamsters, rats and guinea pigs. In addition, the immunoglobulin Fc fragment may be an Fc fragment that is derived from IgG, IgA, IgD, IgE and IgM, or that is made by combinations thereof or hybrids thereof. Preferably, it is derived from IgG or IgM, which is among the most abundant proteins in human blood, and most preferably from IgG, which is known to enhance the half-lives of the ligand-binding proteins. Herein, the immunoglobulin Fc may be obtained from a native immunoglobulin by isolating whole immunoglobulins from human or animal organisms and treating them with a proteolytic enzyme or it may be recombinants or derivatives thereof, obtained from transformed animal cells or microorganisms. Preferable is recombinant human immunoglobulin Fc produced by *E. coli* transformants.

On the other hand, IgG is divided into IgG1, IgG2, IgG3 and IgG4 subclasses, and the present invention includes combinations and hybrids thereof. Preferred are IgG2 and IgG4 subclasses, and most preferred is the Fc fragment of IgG4 rarely having effector functions such as CDC (complement dependent cytotoxicity). That is, as the drug carrier of the present invention, the most preferable immunoglobulin Fc fragment is a human IgG4-derived aglycosylated Fc fragment. The human-derived Fc fragment is more preferable than a non-human derived Fc fragment, which may act as an antigen in the human body and cause undesirable immune responses such as the production of a new antibody against the antigen.

The long-acting G-CSF conjugate useful in the present invention is prepared by linking the G-CSF and the immunoglobulin Fc fragment together. In this regard, the G-CSF and the immunoglobulin Fc fragment may be cross-linked via a non-peptide polymer or may be formed into a fusion protein using a recombinant technique.

The non-peptide polymer for use in cross-linking may be selected from the group consisting of biodegradable polymers, lipid polymers, chitins, hyaluronic acid, and combinations thereof. The biodegradable polymer may be selected from polyethylene glycol, polypropylene glycol, copolymers of ethylene glycol and propylene glycol, polyoxyethylated polyols, polyvinyl alcohol, polysaccharides, dextran, polyvinyl ethyl ether, PLA (poly(lactic acid), PLGA (poly-lactic-glycolic acid), and combinations thereof. Most preferred is poly(ethylene glycol) (PEG), with a preference for polyethylene glycol. Also, derivatives thereof well known in the art and able to be easily prepared within the skill of the art are included in the scope of the present invention.

The long-acting G-CSF conjugates useful in the present invention may be prepared using a genetic engineering technique, as disclosed in Korean Patent No. 10-0725315.

The liquid formation according to the present invention comprises a long-acting G-CSF conjugate in a therapeutically effective amount. Typically, the therapeutically effective amount of G-CSF is about 300 mcg per single-use vial. The concentration of the long-acting G-CSF conjugates used in the present invention is on the order of 7 mg/ml to 22 mg/ml, and preferably on the order of 11 mg/ml to 22.

As used herein, the term "stabilizer" is intended to refer to a substance which allows the long-acting G-CSF conjugate to be safely stored. The term "stabilization" is intended to mean the loss of an active ingredient by up to a predetermined rate, generally, up to 10%, for a certain period of time under a storage condition. When G-CSF retains 90% or more of its original activity and preferably 95% or higher of the original activity after having been stored at 10° C. for 2 years, at 25° C. for 6 months or at 40° C. for one to two weeks, it is understood as being stable. As for proteins such as G-CSF, their storage stability is important in suppressing the potential generation of G-CSF-like antigenic materials as well as guaranteeing accurate administration amounts. During storage, about 10% loss of G-CSF activity may be understood as being permissible for administration unless G-CSF within the formulation aggregates or is fragmented to form antigenic materials.

The stabilizer suitable for use in the present invention comprises a buffered solution formulated to endow the long-acting G-CSF conjugate with stability, and mannitol.

In addition, the stabilizer according to the present invention is preferably free of albumin. Because it is prepared from human blood, human serum albumin, available as a stabilizer for proteins, has the possibility of being contaminated by human-derived pathogenic viruses. Gelatin or bovine serum albumin may cause diseases or induce an allergic reaction in some patients. Free of human- or animal-derived serum albumin or heterogeneous proteins such as purified gelatin, the stabilizer according to the present invention is freed from concerns about viral infection.

The buffer solution in the stabilizer plays a role in keeping the pH of the liquid formulation constant to prevent fluctuations in the pH, thus stabilizing the long-acting G-CSF conjugate. The buffer solution useful in the present invention may comprise pharmaceutically acceptable pH buffering agents including alkaline salts (sodium or potassium phosphate, hydrogen or dihydrogen salts thereof), sodium citrate/citric acid, sodium acetate/acetic acid, and a combination thereof. Suitable for use in the present invention is citrate buffer, phosphate buffer, tartarate buffer, carbonate buffer, succinate buffer, lactate buffer, and acetate buffer, with a preference for phosphate buffer and citrate buffer, citrate buffer being greater preferred. In citrate buffer, citrate ranges in concentration preferably from 5 to 100 mM and more preferably from 10 to 50 mM. The buffer has preferably a pH of 4.0 to 8.0, more preferably a pH of 5.0 to 7.0 and most preferably a pH 5.0 to 6.0.

In an embodiment, the long acting G-CSF conjugate was evaluated for stability according to pH values of the buffer used. At pH 5.5, citrate buffer of pH 5.5 was found to guarantee higher stability to the long-acting G-CSF than at pH 6.0 (see Tables 2 and 4). From these results, it is understood that the long-acting G-CSF conjugate of the present invention is stabilized to different extents depending on the pH values of the buffer and shows peak stability at a certain pH. Particularly, the long-acting G-CSF conjugate in which Fc, stable at neutral pH, is linked to G-CSF was found to be decreased in storage stability when a liquid formulation comprising buffer of low pH. Neulasta, a commercially available PEG-fused G-CSF drug, employs an acetate buffer pH 4 as a stabilizing agent. However, it is not recommended to apply the conventional stabilizer composition and pH to the long-acting G-CSF conjugate not only because the long-acting G-CSF conjugate of the present invention is larger in both molecular weight and volume than the wild-type G-CSF, but also because the immunoglobulin Fc is stable in a neutral pH range.

Mannitol, a kind of sugar alcohol, is used in the stabilizer of the present invention because it acts to enhance the stability of the long-acting G-CSF conjugate. Mannitol is used preferably at a concentration of from 1 to 20% (w/v) based on the total volume of the liquid formulation, more preferably at a concentration of from 3 to 10% (w/v) and most preferably at a concentration of from 5 to 7% (w/v).

In accordance with an embodiment of the present invention, when mannitol in the presence of a citrate buffer was used as a stabilizer, the storage stability of the long-acting G-CSF conjugate was shown to increase more greatly than sorbitol was used (see Table 6). These data show the specificity of mannitol as a stabilizer for the long-acting G-CSF conjugate, compared to other stabilizers, indicating that different stabilizers are needed according to the targets to be stabilized.

The stabilizer may further comprise other sugar alcohols if they do not deteriorate the stabilizing effect of a combination of mannitol and buffer on the long-acting G-CSF conjugate.

In another embodiment of the present invention, the stabilizer useful in the present invention may further comprise at least one component selected from the group consisting of isotonic agents, polyhydric alcohols, sugars, non-ionic surfactants and neutral amino acids, in addition to the buffer solution and mannitol.

The isotonic agent acts not only to maintain a suitable osmotic pressure when the long-acting G-CSF conjugate in the liquid formulation is allowed to enter the body, but to further stabilize the long-acting G-CSF conjugate in the liquid formation. Examples of the isotonic agent include water-soluble inorganic salts. Among them are sodium chloride, sodium sulfate, sodium citrate, calcium chloride, and a combination thereof. Most preferable is sodium chloride.

Preferably, the concentration of the isotonic agent is on the order of 5 to 200 mM. Within this range, the concentration of the isotonic may be adjusted according to the kinds and amounts of the components contained such that the liquid formulation is isotonic.

Preferred examples of the sugar which can be further contained to increase the storage stability of the long-acting G-CSF conjugate include monosaccharides such as mannose, glucose, fucose and xylose, and polysaccharides such as lactose, maltose, sucrose, raffinose and dextran. In the liquid formulation, the sugar is preferably used in an amount of from 1 to 20% (w/v) and more preferably used in an amount of from 5 to 20%(w/v). Examples of the polyhydric alcohol useful in the present invention include propylene glycol, low-molecular weight polyethylene glycol, glycerol, and low-molecular weight polypropylene glycol. They may be used alone or in combination. And their concentration in the liquid formulation is preferably on the order of 1 to 15%(w/v) and more preferably on the order of 5 to 15% (w/v).

As for the non-ionic surfactant, it lowers the surface tension of the protein solution to prevent the proteins from being adsorbed onto or aggregating at hydrophobic surfaces. polysorbate-based non-ionic surfactants and poloxamer-based non-ionic surfactants are suitable for use in the present invention. They may be used alone or in combination. Preferred is polysorbate-based non-ionic surfactants. Among them are polysorbate 20, polysorbate 40, polysorbate 60 and polysorbate 80, with greater preference for polysorbate 80.

It is not recommended to use the non-ionic surfactant in a high concentration because the non-ionic surfactant, if present at a high concentration, induces interference with UV-spectrometry or iso-focusing to make it difficult to evaluate the concentration or stability of protein, accurately. Thus, the liquid formulation of the present invention may comprise the non-ionic surfactant preferably at a concentration of 0.1% (w/v) or less and more preferably at a concentration of from 0.001 to 0.05% (w/v).

With regard to the storage stability of the long-acting G-CSF conjugate, polysorbate 20 was compared to polysorbate 80. The long acting G-CSF conjugate was found to increase in stability in the presence of polysorbate 80, compared to polysorbate 20 (see Table 8). Neulasta, a PEG-fused G-CSF drug formulation, employs polysorbate 20. However, the liquid formulation of the present invention guaranteed higher storage stability to the long-acting G-CSF when containing polysorbate 80 than polysorbate 20. From these data, it is understood that different surfactants are needed according to the targets to be stabilized.

In an embodiment of the present invention, the long-acting G-CSF conjugate was kept more stably for the duration of storage at 40° C. for 4 weeks in a liquid formulation containing as a non-ionic surfactant 0.005% (w/v) polysorbate 80 than 0.01% (w/v) polysorbate 80 (see Table 10).

An amino acid, also available as a stabilizer for the liquid formulation, acts to attract more water molecules around G-CSF in a solution, so that the outermost hydrophilic amino acid molecules of the G-CSF are further stabilized (Wang, Int. J. Pharm. 185: 129-188, 1999). In this regard, charged amino acids may induce electrostatic attraction with G-CSF to promote the aggregation of G-CSF. Hence, neutral amino acids, such as glycine, alanine, leucine and isoleucine, are added as a stabilizing component. In the liquid formulation, the neutral amino acid is used preferably at a concentration of from 0.1 to 10% (w/v).

In an embodiment of the present invention, a stabilizer comprising mannitol at a concentration of from 3 to 12% (w/v) based on the total volume of the liquid formulation allowed the long-acting G-CSF conjugate having a large molecular weight Fc to be stored for 4 weeks with stability even though no neutral amino acids were added (see Table 12). Accordingly, a liquid formulation for providing high stability for long-acting G-CSF conjugates can be prepared using a high concentration of mannitol even when no neutral amino acids are added. However, a mannitol concentration exceeding 20% (w/v) is out of the upper isotonic limit. Thus, mannitol is used at a concentration of from 1 to 20% (w/v) in the liquid formulation, preferably at a concentration of from 3 to 10% (w/v), and more preferably at a concentration of from 5 to 7% (w/v).

In addition to the above-mentioned components including a buffer, an isotonic agent, a sugar alcohol, a neutral amino acid and a non-ionic surfactant, the liquid formulation of the present invention may further selectively comprise other components known in the art so long as they do not deteriorate the effect of the present invention.

According to a preferred embodiment of the present invention, the liquid formulation does not contain albumin and may comprise a buffer solution, mannitol, an isotonic agent and a non-ionic surfactant.

In greater detail, the present invention provides a liquid formulation which comprises a long-acting G-CSF conjugate, and a stabilizer, the stabilizer comprising phosphate or citrate buffer, mannitol, an isotonic agent and polysorbate 80, the isotonic agent being selected from the group consisting of sodium chloride, sodium sulfate, sodium citrate and a combination thereof.

Preferably, the liquid formulation comprises a phosphate or citrate buffer solution ranging in concentration of from 5 to 100 mM and in pH from 5 to 7, mannitol at a concentration of from 1 to 20% (w/v), an isotonic agent at a concentration of from 5 to 200 mM, the isotonic agent being selected from the group consisting of sodium chloride, sodium sulfate and sodium citrate, and polysorbate 80 at a concentration of from 0.001 to 0.05% (w/v). More preferably, the liquid formulation comprises a citrate buffer solution ranging in concentration of from 5 to 100 mM and in pH from 5 to 6, mannitol at a concentration of from 1 to 10% (w/v), sodium chloride at a concentration of from 100 to 200 mM, and polysorbate 80 at a concentration of from 0.001 to 0.05% (w/v). Most preferably, the liquid formulation comprises a citrate buffer (pH 5.2-5.8) at a concentration of 20 mM, mannitol at a concentration of from 3 to 7% (w/v), sodium at a concentration of from 100 to 200 mM, and polysorbate 80 at a concentration of from 0.001 to 0.05% (w/v), and no neutral amino acids are used therein.

In an embodiment of the present invention, a liquid formulation for long-acting G-CSF conjugates comprising a Na-citrate buffer solution (pH 5.5), 5% (w/v) mannitol, 150 mM sodium chloride and 0.005% (w/v) polysorbate 80 was compared with the known G-CSF formulation Neulasta, Amgen, for the storage stability of G-CSF. G-CSF was found to be more stable in the liquid formulation of the present invention than in the commercially available one comprising sodium citrate of pH 4 (see Table 14).

In another embodiment, the liquid formulation for long-acting G-CSF conjugates comprising a citrate buffer of pH 5.5, mannitol, sodium chloride and polysorbate 80 in accordance with the present invention was assayed for long-term storage stability and found to keep the long-acting G-CSF conjugates stably for 6 months and guarantee at least 96.6% of the activity even after 6-month storage under an accelerated condition (see Table 16).

From the data, it is understood that the liquid formulation comprising buffer ranging in pH from 5 to 6 and mannitol at a concentration of from 1 to 20% (w/v) can store long-acting G-CSF conjugate therein stably for 12 months or longer.

Advantageous Effects

As described above, the stabilizer comprising buffer and mannitol in accordance with the present invention is specialized for long-acting G-CSF conjugates. Being free of human serum albumin and other potential factors harmful to the body, the liquid formulation for long-acting G-CSF conjugates in accordance with the present invention is freed from concerns about viral infections and guarantees excellent storage stability to the long-acting G-CSF conjugates in which G-CSF and immunoglobulin Fc fragment are linked and which are greater in molecular weight and longer in the duration of action than natural forms of G-CSF.

DESCRIPTION OF DRAWINGS

FIG. 1 is a graph showing the stability of G-CSF in liquid formulations for long-acting G-CSF conjugate where buffers with different pH values are used and in the PEG-fusion G-CSF formulation Neulasta, when they are analyzed using SE-HPLC every week for the duration of storage at 40° C. for two weeks.

MODE FOR INVENTION

A better understanding of the present invention may be obtained through the following examples which are set forth to illustrate, but are not to be construed as limiting the present invention.

Example 1

Construction of Long-Acting G-CSF Conjugate

<1-1> Preparation of Immunoglobulin Fc Fragment Using Immunoglobulin

The immunoglobulin Fc fragment useful in the present invention was human aglycosylated IgG4 Fc fragment which could be expressed from the E. coli transformant as disclosed in Korean Patent No. 725314.

<1-2> Preparation of Recombinant Human Granulocyte-Colony Stimulating Factor

The recombinant human G-CSF used in this example is a mutant one ($^{17}$Ser-G-CSF) in which a serine residue was located at position 17, instead of cysteine for the wild-type, and could be expressed from the E. coli transformant as disclosed in Korean Patent No. 356140.

<1-3> Preparation of Long-Acting G-CSF Conjugate Using Immunoglobulin Fc Fragment The long-acting G-CSF conjugate in this example was a construct in which a human granulocyte-colony stimulating factor and an immunoglobulin Fc fragment is covalently linked by a non-peptide polymer. And it was obtained as disclosed in Korean Patent No. 725315 and 775343.

Example 2

Assay of Long-Acting G-CSF Conjugates for Stability According to the pH of the Buffer To formulate a liquid formulation for stabilizing the G-CSF conjugate prepared in Example 1, an examination was made of the effect that varying the pH values of the buffer had on the stability of the long-acting G-CSF conjugate.

For the assay, liquid formulations for the long-acting G-CSF conjugate of Table 1 were prepared with stabilizer compositions comprising mannitol as a stabilizing agent, polysorbate 80 as a surfactant, and a sodium citrate solution with a pH of 5.0, 5.5 or 6.0 as a buffer. After they were stored at 40° C. for two week, size exclusion chromatography was preformed for analysis. The results are summarized in Table 2, below. The retention rate of the long-acting G-CSF conjugate compared to the initial value thereof was expressed as SE-HPLC (%).

TABLE 1

|   | G-CSF | Buffer | Salt | Stabilizing Agent | Surfactant |
| --- | --- | --- | --- | --- | --- |
| 1 | 6 mg/mL | 20 mM Na-Citrate, pH 5.0 | 150 mM NaCl | 5% Mannitol | 0.01% Polysorbate 80 |
| 2 | 6 mg/mL | 20 mM Na-Citrate, pH 5.5 | 150 mM NaCl | 5% Mannitol | 0.01% Polysorbate 80 |

TABLE 1-continued

| G-CSF | Buffer | Salt | Stabilizing Agent | Surfactant |
|---|---|---|---|---|
| 3 | 6 mg/mL | 20 mM Na-Citrate, pH 6.0 | 150 mM NaCl | 5% Mannitol | 0.01% Polysorbate 80 |

TABLE 2

| | SE-HPLC (%) | | |
|---|---|---|---|
| | Start | Week 1 | Week 2 |
| 1 | 100 | N.A | N.A |
| 2 | 100 | 94.9 | 94.6 |
| 3 | 100 | 90.6 | 89.8 |

As is apparent from the data of Table 2, a sodium citrate buffer at a pH of 5.0 causes the precipitation of the protein on Week 1 while no precipitates were detected when a sodium citrate buffer at a pH of 5.5 or 6.0 was used. It was also understood that stability of the long-acting G-CSF was further increased in a sodium citrate buffer having a pH of 5.5 than a pH of 6.0.

The following experiment was performed with buffers having subdivided pH values. Liquid formulations for long-acting G-CSF conjugates were prepared with the stabilizer compositions set in Table 3, below and stored at 40° C. for two weeks before being analyzed using reverse phase chromatography and size exclusion chromatography (SE-HPLC). The results are summarized in Table 4, below. The retention rate of the long-acting G-CSF conjugate compared to the initial value thereof was expressed as SE-HPLC (%).

TABLE 3

| | G-CSF | Buffer | Salt | Stabilizing Agent | Surfactant |
|---|---|---|---|---|---|
| 1 | 6 mg/mL | 20 mM Na-Citrate, pH 5.5 | 150 mM NaCl | 5% Mannitol | 0.005% Polysorbate 80 |
| 2 | 6 mg/mL | 20 mM Na-Citrate, pH 5.2 | 150 mM NaCl | 5% Mannitol | 0.005% Polysorbate 80 |
| 3 | 6 mg/mL | 20 mM Na-Citrate, pH 5.8 | 150 mM NaCl | 5% Mannitol | 0.005% Polysorbate 80 |

TABLE 4

| | RP-HPLC (%) | | | SE-HPLC (%) | | |
|---|---|---|---|---|---|---|
| | Start | Week 1 | 2 Week | Start | 1 Week | 2 Week |
| 1 | 100 | 95.5 | 90.4 | 100 | 95.4 | 90.5 |
| 2 | 100 | 95.8 | 91.9 | 100 | 96.4 | 94.4 |
| 3 | 100 | 95.7 | 91.8 | 100 | 93.8 | 89.8 |

After storage for two weeks in sodium citrate buffers with pHs of 5.2 to 5.5, as seen in Table 4, the long-acting G-CSF conjugate was found to retain about 90% or higher of the initial activity.

From the results, it is understood that the long-acting G-CSF conjugates according to the present invention are stabilized to different extents depending on the pH values of the buffer used, with peak stability in a certain pH range. Particularly, storage stability of the long-acting G-CSF conjugate in which Fc, stable at neutral pH, is linked to G-CSF was found to be decreased in a liquid formulation comprising buffer of low pH.

Example 3

Assay of Long-Acting G-CSF Conjugates for Stability According to Sugar Alcohols

Sugar alcohols such as sorbitol and mannitol were assayed for ability to stabilize the long-acting G-CSF conjugate, as follows.

Liquid formulations for long-acting G-CSF conjugates were prepared with stabilizer compositions which comprised mannitol or sorbitol as a sugar alcohol, sodium chloride as an isotonic agent, and polysorbate as a surfactant, as set in Table 5, below, and were stored at 40° C. for four weeks before being analyzed using size exclusion chromatography (SE-HPLC). The results are summarized in Table 6, below. The retention rate of the long-acting G-CSF conjugate compared to the initial value thereof (area %/initial area %) was expressed as SE-HPLC (%).

TABLE 5

| | G-CSF | Buffer | Salt | Stabilizing Agent | Surfactant |
|---|---|---|---|---|---|
| 1 | 3 mg/mL | 20 mM Na-Citrate, pH 6.0 | 100 mM NaCl | 5% Mannitol | 0.01% Polysorbate 80 |
| 2 | 3 mg/mL | 20 mM Na-Citrate, pH 6.0 | 100 mM NaCl | 5% Sorbitol | 0.01% Polysorbate 80 |

TABLE 6

| | SE-HPLC (%) | | | |
|---|---|---|---|---|
| | Start | Week 1 | Week 2 | Week 4 |
| 1 | 100 | 97.9 | 97.3 | 93.7 |
| 2 | 100 | 100 | 96.6 | 90.7 |

As is apparent from the data of Table 6, the use of mannitol instead of sorbitol as a stabilizing agent kept the long-acting G-CSF conjugate more stable.

Example 4

Assay of Long-Acting G-CSF Conjugates for Stability According to Kind of Non-Ionic Surfactant In the presence of a sodium citrate buffer, various non-ionic surfactants were assayed for their ability to stabilize the long-acting G-CSF conjugate, as follows.

For the assay, comparison was made between two non-ionic surfactants, polysorbate 80 and polysorbate 20, the latter being contained in Neulasta, a commercially available liquid formulation of PEG fusion G-CSF. Other agents including sodium citrate buffer pH 5.5 and mannitol, which were shown to provide stability for the long-acting G-CSF conjugate in Examples 2 and 3, were employed in the proper combination. Liquid formulations for long-acting G-CSF conjugate were prepared with stabilizer compositions which comprised different kinds of polysorbate as set in Table 7, below, and were stored at 40° C. for four weeks before being analyzed using size exclusion chromatography (SE-HPLC). The results are summarized in Table 8, below. The retention rate of the long-acting G-CSF conjugate compared to the initial value thereof was expressed as SE-HPLC (%).

TABLE 7

| G-CSF | Buffer | Salt | Stabilizing Agent | Surfactant |
|---|---|---|---|---|
| 1 6 mg/mL | 20 mM Na-Citrate, pH 5.5 | 150 mM NaCl | 5% Mannitol | 0.005% Polysorbate 20 |
| 2 6 mg/mL | 20 mM Na-Citrate, pH 5.5 | 150 mM NaCl | 5% Mannitol | 0.005% Polysorbate 80 |

TABLE 8

| | SE-HPLC (%) | | | |
|---|---|---|---|---|
| | Start | Week 1 | Week 2 | Week 4 |
| 1 | 100 | 95.6 | 94.6 | 85.0 |
| 2 | 100 | 95.4 | 95.8 | 92.4 |

Under the same conditions, as seen in Table 8, polysorbate 80 guaranteed higher storage stability to the long-acting G-CSF conjugate than did polysorbate 20. No significant differences in the storage stability of the long-acting G-CSF between the two were detected until the end of two week storage at 40° C. However, On Week 4, the non-ionic surfactants exhibited significant differences in the storage stability although they are very similar in structure.

Example 5

Assay of Long-Acting G-CSF Conjugates for Stability in Relation to the Concentration of Non-Ionic Surfactant In Example 4, polysorbate 80 was evaluated as being more effective in stabilizing the long-acting G-CSF than polysorbate 20. In this example, an examination was made of the effect of the concentration of polysorbate 80 on the stability of the long-acting G-CSF conjugate. To this end, liquid formulations for long-acting G-CSF conjugate were prepared with the stabilizer compositions set in Table 9, below, and were stored at 40° C. for four weeks before being analyzed using size exclusion chromatography. The results are summarized in Table 10, below. The retention rate of the long-acting G-CSF conjugate compared to the initial value thereof was expressed as SE-HPLC (%).

TABLE 9

| G-CSF | Buffer | Salt | Stabilizing Agent | Surfactant |
|---|---|---|---|---|
| 1 6 mg/mL | 20 mM Na-Citrate, pH 5.5 | 150 mM NaCl | 5% Mannitol | 0.005% Polysorbate 80 |
| 2 6 mg/mL | 20 mM Na-Citrate, pH 5.5 | 150 mM NaCl | 5% Mannitol | 0.01% Polysorbate 80 |

TABLE 10

| | SE-HPLC (%) | | | |
|---|---|---|---|---|
| | Start | week 1 | week 2 | week 4 |
| 1 | 100 | 95.4 | 95.8 | 92.4 |
| 2 | 100 | 94.9 | 95.3 | 85.1 |

For the duration of storage of four weeks at 40° C., as shown in Table 10, the long-acting G-CSF conjugate was found to be more stable in a liquid formulation comprising 0.005% polysorbate 80 than one with 0.01% polysorbate 80.

Example 6

Assay of Long-Acting G-CSF Conjugates for Stability in Relation to Amino Acid

The use of an amino acid as a stabilizing agent was assayed for its ability to stabilize long-acting G-CSF conjugates. An experiment for evaluating the storage stability of the long-acting g-CSF was performed with stabilizers comprising sodium citrate buffer (pH 6.0), mannitol and the neutral amino acid glycine.

Liquid formulations for long-acting G-CSF conjugates were prepared with stabilizer compositions set out in Table 11, below, and were stored at 40° C. for four weeks before being analyzed using size exclusion chromatography. The results are summarized in Table 12, below. The retention rate of the long-acting G-CSF conjugate compared to the initial value (area %/initial area %) thereof was expressed as SE-HPLC (%).

TABLE 11

| G-CSF | Buffer | Salt | Stabilizing Agent | Surfactant |
|---|---|---|---|---|
| 1 10 mg/mL | 20 mM Na-Citrate, pH 6.0 | 100 mM NaCl | 5% Mannitol | 0.01% Polysorbate 80 |
| 2 10 mg/mL | 20 mM Na-Citrate, pH 6.0 | 100 mM NaCl | 5% Mannitol, 10 mM Glycine | 0.01% Polysorbate 80 |
| 3 10 mg/mL | 20 mM Na-Citrate, pH 6.0 | 100 mM NaCl | 5% Sorbitol | 0.01% Polysorbate 80 |

TABLE 12

| | SE-HPLC (%) | | | |
|---|---|---|---|---|
| | Start | Week 1 | Week 2 | Week 4 |
| 1 | 100 | 97.9 | 97.3 | 93.7 |
| 2 | 100 | 98.2 | 97.3 | 93.4 |
| 3 | 100 | 100 | 96.6 | 90.7 |

Even in the absence of the neutral amino acid glycine, as seen in Table 12, the liquid formulation comprising a high concentration (5% (w/v)) of mannitol guaranteed the storage stability of the long-acting conjugate at a level similar to that obtained when the neutral amino acid was used.

Example 7

Comparison of Storage Stability of Long-Acting G-CSF Conjugates Between Liquid Formulations With regard to storage stability, the liquid formulation which was prepared with a stabilizer composition comprising sodium citrate buffer (pH 5.5), sodium chloride, mannitol and polysorbate 80, all proven in Examples 2 to 6 to have stabilizing ability, was compared with the commercially available G-CSF liquid formulation Neulasta, Amgen. The compositions of the liquid formulation of the present invention and Neulasta are shown in Table 13, below. While being stored at 40° C. for two weeks, the liquid formulations for long-acting G-CSF conjugate were analyzed every week using reverse phase chromatography and size exclusion chromatography. The results are summarized in Table 14, below. The retention rate of the long-acting G-CSF conjugate compared to the initial value thereof was expressed as RP-HPLC (%) and SE-HPLC (%).

TABLE 13

|  | Conc. | Buffer | Salt | Stabilizing Agent | Surfactant |
|---|---|---|---|---|---|
| Neulasta | 6 mg/ 0.6 mL | 10 mM Na-acetate (pH 4.0) | — | 5% Sorbitol | 0.003% Polysorbate 20 |
| Long-Acting G-CSF | G-CSF 6 mg/mL | 20 mM Na-Citrate (pH 5.5) | 150 mM NaCl | 5% Mannitol | 0.005% Polysorbate 80 |

TABLE 14

|  | RP-HPLC (%) | | | SE-HPLC (%) | | |
|---|---|---|---|---|---|---|
|  | Start | Week 1 | Week 2 | Start | Week 1 | Week 2 |
| Neulasta | 100 | 99.7 | 97.7 | 100 | 98.4 | 94.8 |
| Long-Acting G-CSF | 100 | 98.5 | 97.5 | 100 | 96.9 | 95.8 |

After long-term storage, as is apparent from the data of Table 14, the liquid formulation for long-acting G-CSF conjugate of the present invention guaranteed storage stability equivalent to or greater than that provided by Neulasta. From these results, it is understood that the liquid formulations of the present invention are capable of guaranteeing excellent storage stability specifically to the long-acting G-CSF conjugate.

Example 8

Assay of Liquid Formulations for Long-Acting G-CSF Conjugate for Long-Term Storage Stability and Accelerated Stability To examine the long-term storage stability and accelerated stability thereof, the liquid formulation for long-acting G-CSF conjugate, prepared from a stabilizer composition comprising sodium citrate buffer (pH 5.5), sodium chloride, mannitol and polysorbate 80, which was proven to guarantee the most storage stability in Examples 2 to 6, was stored at 4° C. for 12 months and subsequently at 25° C. for 6 months during which samples were analyzed for storage stability. The results are summarized in Table 15 and 16, below. In Table 15 and 16, the retention rate of the long-acting G-CSF conjugate compared to the initial value thereof was expressed as RP-HPLC (%), SE-HPLC (%), protein content (%) and biological inert activity (%).

TABLE 15

Assay for Long-Term Storage Stability (Storage at 4° C.)

| Storage Term | Properties | pH | Identification Test | | Purity Test | | | | Protein Content Test (%) | Biological Inert Activity (%) |
|---|---|---|---|---|---|---|---|---|---|---|
|  |  |  | RP-HPLC | Western Blot | SDS-PAGE | RP-HPLC (%) | SE-HPLC (%) |  |  |  |
| Start | Colorless transparent | 5.5 | Agreed | Suitable | Suitable | 100.0 | 100.0 | | 100.0 | 100.0 |
| 3 Months | Colorless transparent | 5.5 | Agreed | Suitable | Suitable | 100.1 | 101.1 | | N.A | 120.5 |
| 6 Months | Colorless transparent | 5.5 | Agreed | Suitable | Suitable | 99.6 | 102.0 | | N.A | 102.3 |
| 9 Months | Colorless transparent | 5.5 | Agreed | Suitable | Suitable | 99.5 | 101.6 | | N.A | 86.4 |
| 12 Months | Colorless transparent | 5.5 | Agreed | Suitable | Suitable | 100.0 | 101.6 | | N.A | 81.1 |

TABLE 16

Accelerated Stability Assay (Storage at 25° C.)

| Storage Term | Properties | pH | Identification Test | | Purity Test | | | Protein Content Test (%) | Biological Inert Activity (%) |
|---|---|---|---|---|---|---|---|---|---|
|  |  |  | RP-HPLC | Western Blot | SDS-PAGE | RP-HPLC (%) | SE-HPLC (%) |  |  |
| Start | Colorless transparent | 5.5 | Agreed | Suitable | Suitable | 100.0 | 100.0 | 100.0 | 100.0 |
| 2 Months | Colorless transparent | N.A | Agreed | Suitable | Suitable | 100.2 | 99.0 | N.A | 75.0 |
| 4 Months | Colorless transparent | N.A | Agreed | Suitable | Suitable | 98.4 | 100.4 | N.A | 78.0 |
| 6 Months | Colorless transparent | 5.5 | Agreed | Suitable | Suitable | 96.6 | 99.7 | 100.9 | 81.8 |

As is apparent from the data of Table 15 and 16, the long-acting G-CSF conjugate was kept highly stable for 6 months in the liquid formulation comprising the stabilizer composition according to the present invention and was found to have 92.5% of the initial activity even after storage for 6 months in the liquid formulation under the accelerated condition. Therefore, the liquid formulation for long-acting G-CSF conjugate according to the present invention exhibits effective storage stability.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

INDUSTRIAL APPLICABILITY

Being free of human serum albumin, the liquid formulation for guaranteeing storage stability specifically to long-acting G-CSF conjugates in accordance with the present invention is free from concerns about viral infections. It comprises a simple composition, thus having an economical advantage over other stabilizers or freeze-dried formulations. In addition, because it contains a long-acting G-CSF conjugate which has a longer duration of action than a natural form as well as keeping the protein activity high over a long period of time, the liquid formulation can be used as an effective drug system.

The invention claimed is:

1. A liquid formulation for a long-acting granulocyte-colony stimulating factor (G-CSF) conjugate, comprising
    a therapeutically effective amount of a long-acting granulocyte-colony stimulating factor conjugate in which G-CSF is covalently linked to an immunoglobulin Fc fragment via a non-peptide polymer or peptide linker and the immunoglobulin Fc fragment is not modified with other non-peptide polymer, and
    an albumin-free stabilizer containing citrate buffer of pH 5.5 to 8.0, polysorbate 80 and mannitol,
    wherein G-CSF is a wild type human G-CSF or a human $^{17}$Ser-G-CSF mutant in which cystein at position 17 of the wild type human G-CSF is substituted with serine, and
    wherein a concentration of the mannitol ranges from 1 to 20% (w/v) based on the total volume of the liquid formulation.

2. The liquid formulation according to claim 1, wherein a concentration of the buffer ranges from 5 to 100 mM.

3. The liquid formulation according to claim 1, wherein the albumin-free stabilizer further comprises an ingredient selected from the group consisting of an isotonic agent, a polyhydric alcohol, a sugar, a neutral amino acid, and a combination thereof.

4. The liquid formulation according to claim 3, wherein the isotonic agent is a salt selected from the group consisting of sodium chloride, sodium sulfate, sodium citrate and a combination thereof.

5. The liquid formulation according to claim 3, wherein a concentration of the isotonic agent ranges from 5 to 200 mM.

6. The liquid formulation according to claim 1, wherein a concentration of polysorbate 80 ranges from 0.001 to 0.05% (w/v) based on the total volume of the liquid formulation.

7. The liquid formulation according to claim 3, wherein the neutral amino acid is selected from the group consisting of glycine, alanine, leucine, isoleucine, and a combination thereof.

8. The liquid formulation according to claim 3, wherein a concentration of the neutral amino acid ranges from 0.1 to 10%(w/v) in the liquid formulation.

9. The liquid formulation according to claim 1, wherein the albumin-free stabilizer comprises a citrate buffer ranging in pH from 5.5 to 8 and in concentration from 5 to 100 mM, mannitol at a concentration of from 1 to 20%(w/v), sodium chloride at a concentration of from 5 to 200 mM, and polysorbate 80 at a concentration of from 0.001 to 0.05%.

10. The liquid formulation according to claim 1, wherein a concentration of the G-CSF ranges from 71 to 2230 mg/mL of the formulation.

11. The liquid formulation according to claim 1, wherein the immunoglobulin Fc fragment is selected from the group consisting of IgG, IgA, IgD, IgE, IgM and a combination thereof.

12. The liquid formulation according to claim 11, wherein the immunoglobulin Fc fragment is a hybrid fragment composed of domains of different origins from the group consisting of IgG, IgA, IgD, IgE and IgM.

13. The liquid formulation according to claim 11, the immunoglobulin Fc fragment is in a form of a dimer or a multimer of single-chain immunoglobulins composed of domains of the same origin.

14. The liquid formulation according to claim 11, wherein the immunoglobulin Fc fragment is an IgG4 Fc fragment.

15. The liquid formulation according to claim 14, wherein the immunoglobulin Fc fragment is a human aglycosylated IgG4 Fc fragment.

16. The liquid formulation according to claim 1, wherein the non-peptide polymer is selected from the group consisting of a biodegradable polymer, a lipid polymer, chitin, hyaluronic acid, and a combination thereof.

17. The liquid formulation according to claim 16, wherein the biodegradable polymer is selected from the group consisting of polyethylen glycol, polypropylene glycol, a copolymer of ethylene glycol and propylene glycol, polyoxyethylated polyols, polyvinyl alcohol, polysaccharides, dextran, polyvinyl ethylether, polylactic acid and polylactic-glycolic acid.

* * * * *